(12) United States Patent
Giannakopulos

(10) Patent No.: US 8,952,322 B2
(45) Date of Patent: Feb. 10, 2015

(54) FAIMS APPARATUS AND METHOD COMPRISING AN ION SEPARATION CHANNEL OF HELICAL SHAPE

(75) Inventor: Anastassios Giannakopulos, Bremen (DE)

(73) Assignee: Thermo Fisher Scientific (Bremen) GmbH, Bremen (DE)

( * ) Notice: Subject to any disclaimer, the term of this patent is extended or adjusted under 35 U.S.C. 154(b) by 20 days.

(21) Appl. No.: 13/822,834

(22) PCT Filed: Sep. 8, 2011

(86) PCT No.: PCT/EP2011/065585
§ 371 (c)(1),
(2), (4) Date: Mar. 13, 2013

(87) PCT Pub. No.: WO2012/038268
PCT Pub. Date: Mar. 29, 2012

(65) Prior Publication Data
US 2013/0180893 A1     Jul. 18, 2013

(30) Foreign Application Priority Data

| Sep. 20, 2010 | (GB) | 1015783.2 |
| Sep. 20, 2010 | (GB) | 1015785.7 |
| Sep. 20, 2010 | (GB) | 1015786.5 |
| Sep. 20, 2010 | (GB) | 1015787.3 |

(51) Int. Cl.
*H01J 49/02* (2006.01)
*B03C 3/00* (2006.01)
*G01N 27/62* (2006.01)

(52) U.S. Cl.
CPC ............... *B03C 3/00* (2013.01); *G01N 27/624* (2013.01)

USPC .................... 250/281; 250/282; 250/283

(58) Field of Classification Search
CPC ............................................... B01D 59/44
USPC ............................................... 250/281
See application file for complete search history.

(56) References Cited

U.S. PATENT DOCUMENTS

| 6,713,758 B2 | 3/2004 | Guevremont et al. |
| 7,034,286 B2 | 4/2006 | Guevremont et al. |

(Continued)

FOREIGN PATENT DOCUMENTS

| GB | 2 327 531 B | 6/2002 |
| GB | 2457556 A | 8/2009 |
| WO | WO 01/69216 A2 | 9/2001 |

OTHER PUBLICATIONS

Hisashi Matsuda, "Electrostatic Analyzer with Variable Focal Length," The Review of Scientific Instruments (1961), vol. 32, (7), pp. 850-852.

(Continued)

*Primary Examiner* — Phillip A Johnston
(74) *Attorney, Agent, or Firm* — Thomas F. Cooney

(57) ABSTRACT

A method and apparatus for high resolution separation of ions based on their high field and low-field mobility properties is described.

An elongate ion separation channel is defined by a plurality of channel walls. First and second channel walls have first and second spaced ion separation electrode assemblies respectively. A power supply applies a periodic asymmetric potential to one or both of the electrode assemblies so as to generate a periodically asymmetric electric field in the channel for ion mobility separation. The channel walls define an ion separation channel of substantially helical shape.

22 Claims, 17 Drawing Sheets

(56) References Cited

U.S. PATENT DOCUMENTS

| | | | |
|---|---|---|---|
| 7,034,289 B2 | 4/2006 | Guevremont et al. | |
| 7,186,972 B2* | 3/2007 | Farnsworth | 250/287 |
| 7,223,967 B2 | 5/2007 | Guevremont et al. | |
| 7,368,709 B2 | 5/2008 | Guevremont | |
| 7,468,511 B2 | 12/2008 | Belford | |
| 7,595,487 B2* | 9/2009 | Fedorov | 250/288 |
| 7,683,315 B2 | 3/2010 | Belford et al. | |
| 7,705,296 B2* | 4/2010 | Wu | 250/282 |
| 2005/0242279 A1 | 11/2005 | Verentchikov | |
| 2010/0264306 A1 | 10/2010 | Rorrer, III et al. | |
| 2011/0168882 A1* | 7/2011 | Hoyes | 250/283 |
| 2011/0253890 A1 | 10/2011 | Belford et al. | |
| 2012/0153140 A1* | 6/2012 | Makarov | 250/282 |
| 2013/0306860 A1 | 11/2013 | Prasad et al. | |

OTHER PUBLICATIONS

Matsuda et al., "Potential Distribution in a Cylindrical Condenser Terminated by Matsuda Plates," International Journal of Mass Spectrometry and Ion Physics, 16 (1975). pp. 395-404.

* cited by examiner

Carrier gas

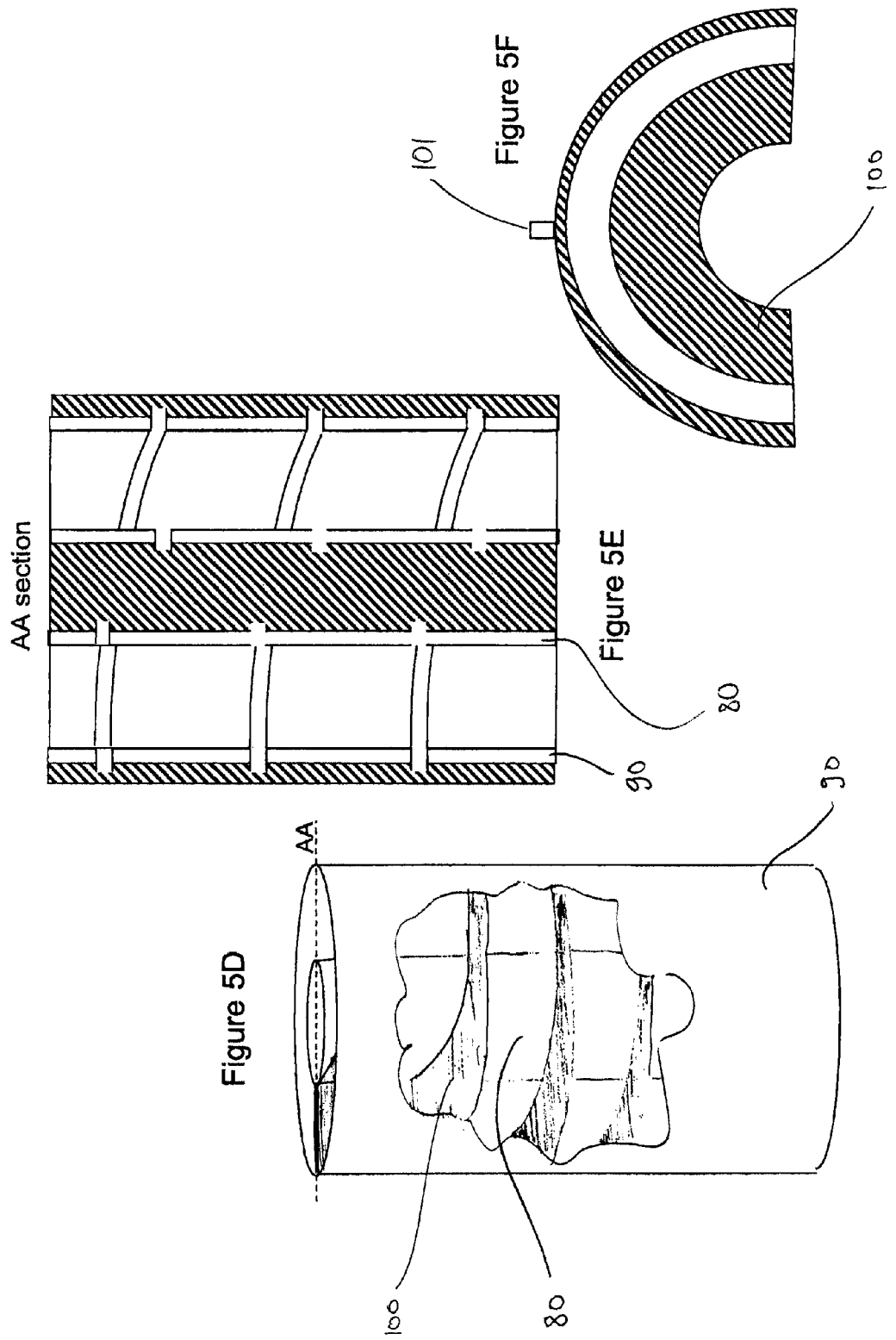

FAIMS APPARATUS AND METHOD COMPRISING AN ION SEPARATION CHANNEL OF HELICAL SHAPE

The invention relates generally to High Field Asymmetric Waveform Ion Mobility Spectrometry (FAIMS). In particular, the invention relates to methods and apparatus for high-resolution separation of ions based on their high-field and low-field mobility properties.

It is known to use parallel plate electrodes in a FAIMS device (see FIG. 1). It is also known to use concentric curved electrodes such as inner and outer cylindrical electrodes for producing a two-dimensional atmospheric pressure ion focusing effect (see FIG. 2A). With the application of an appropriate combination of dispersion voltage (DV) and compensation voltage (CV) an ion of interest is focused into a band-like region in the annular gap between the cylindrical electrodes as a result if the electric fields which change with radial distance. Focusing the ions of interest has the effect of reducing the number of ions of interest that are lost as a result of the ion suffering a collision with one of the inner and outer electrodes.

Other alternative arrangements include a dome-shaped FAIMS analyser (e.g. as described by Alexandre A. Schwartzburg: Differential Ion Mobility Spectrometry, Boca Raton 2009, ISBN 978-1-4200-5106-3, chapter 4.3.10), as shown in FIG. 2B. The domed-FAIMS analyser includes a cylindrical inner electrode having a curved surface terminus proximate an ion outlet orifice of the FAIMS analyser region. The curved surface is substantially continuous with the cylindrical shape of the inner electrode and is aligned co-axially with the ion outlet orifice.

WO 01/69216 describes a so-called "perpendicular-gas-flow-FAIMS", which is identically referred to as a side-to-side FAIMS. The analyzer region of the side-to-side FAIMS is defined by an annular space between inner and outer cylindrical electrodes. In particular, ions that are introduced into the analyzer region of the side-to-side FAIMS are selectively transmitted in a direction that is generally around the circumference of the inner electrode. For instance, the ion inlet and the ion outlet of a side-to-side FAIMS device are disposed, one opposing the other, within a surface of the outer electrode such that ions are selectively transmitted through the curved analyzer region between the ion inlet and the ion outlet along a continuously curving ion flow path absent a portion having a substantially linear component. In particular, the ions travel from the ion inlet to the ion outlet by flowing around the inner electrode in one of a "clock-wise" and a "counter clock-wise" direction. This is in contrast to the above-mentioned FAIMS devices in which the ions are selectively transmitted along the length of the inner electrode.

Of course, the side-to-side FAIMS device has some limitations. For example, ion separation occurs only within a very small portion of the analyzer region of a side-to-side FAIMS. With only two possible ion flow directions through the analyzer region, the ion concentration at a point along either ion flow direction remains relatively high. As the ions transit the analyzer region, diffusion and ion-ion repulsion forces cause the ions to spread out in a direction along the length of the inner and outer electrodes. Accordingly, the ions are introduced through the ion inlet as an approximately collimated beam of ions, but rapidly spread out to form a sheet of ions that travels around the inner electrode to the ion outlet. Furthermore, ions are focused between the inner and outer electrodes as a result of the application of the applied CV and DV, but this focusing occurs only in a direction that is approximately normal to the electrode surfaces, i.e. in a radial direction. As such, there is no force capable of focusing the ions in a direction that is parallel to the electrode surfaces, i.e. in a longitudinal direction. Since the ions spread out slightly during separation, some of the ions become entrained in portions of the analyzer region where the gas flow rate is low or stagnant. Consequently the ion transmission efficiency from the FAIMS to, for example, an external mass spectrometer is reduced.

Additionally, the strength of the focusing field between the inner and outer electrodes is related to the radius of the cylindrically shaped inner electrode. In order to produce stronger focusing fields, it is necessary to utilize an inner electrode with a smaller radius. Of course, a FAIMS analyzer having a smaller inner electrode also has a smaller available volume for separating ions. The distance between the ion inlet orifice and the ion outlet orifice is also smaller, and may result in insufficient ion transit times to effect separation of a mixture that contains different ionic species having similar high field ion mobility properties.

WO 03/067236 discloses a side-to-side FAIMS device with a single inner electrode and a segmented outer electrode in which three electrode segments are electrically isolated from one another (see FIGS. 3A and 3B). The top segment has a first offset DC voltage applied to it. The middle segment has a second offset DC voltage applied to it and the bottom segment has a third offset DC voltage applied to it. The first and third offset DC voltages may be the same. The ions with the appropriate properties for transmission for a given set of applied experimental conditions are confined in a radial direction between the middle outer electrode segment and the inner electrode.

The present invention provides for further improvements in the field of FAIMS which enable increased sensitivity and throughput.

SUMMARY OF INVENTION

Against this background, there is provided an apparatus for separating ions comprising:

an elongate ion separation channel defined by a plurality of channel walls for constraining ions within the said channel, a first channel wall comprising a first ion separation electrode assembly and a second channel wall comprising a second ion separation electrode assembly and being spaced from the said first ion separation electrode assembly in a direction transverse to a direction of elongation of the channel; and a power supply for applying a periodic asymmetric potential to at least one of the first and second ion separation electrode assemblies in order to generate a periodically asymmetric electric field in the channel such that ions flow along the direction of elongation of the channel and are caused to separate according to differential ion mobility;

wherein the ion separation channel walls define an ion separation channel which is substantially of helical shape.

This allows the advantage of curved inner and curved outer electrodes to be combined with an increased ion flow path which results from the helical shaped separation channel. The increased ion flow path increases sensitivity.

In a further aspect of the disclosure, there is provided a method for separating ions comprising:

directing ions in a gas flow through an ion separation channel of substantially helical shape, the channel being formed between first and second ion separation electrode assemblies spaced apart from each other; and applying a periodic asymmetric potential to at least one of the first and second ion separation electrode assemblies such that the ions become separated by differential ion mobility in a periodically asymmetric electric field applied between the first and second ion separation electrode assemblies as a consequence of the asymmetric potential.

This allows the advantage of increased ion flow path and increased sensitivity.

Further aspects of the disclosure are set out in the following numbered clauses:

2.1. A high-field asymmetric waveform ion mobility separation apparatus comprising:

an elongate ion separation channel defined by a plurality of channel walls for constraining ions within the said channel, a first channel wall comprising a first ion separation electrode assembly and a second channel wall comprising a second ion separation electrode assembly;

a power supply for applying a periodic asymmetric potential to at least one of the first and second ion separation electrode assemblies in order to generate a periodically asymmetric electric field in the channel such that ions flow along the direction of elongation of the channel and are caused to separate according to differential ion mobility;

wherein a length of the first ion separation electrode assembly and a length of the second ion separation electrode assembly each extend in a direction substantially parallel to the direction of elongation of the channel and a width of the first ion separation electrode assembly and a width of the second ion separation electrode assembly each extends in a plane orthogonal to the direction of elongation of the channel and wherein a distance separating the said first and second ion separation electrode assemblies varies along the width of the first and second ion separation electrode assemblies in that plane.

Advantageously, this provides an element of ion focusing in the said plane not only in a direction substantially perpendicular to the first and/or second ion separation electrode assemblies (or perpendicular to a tangent to the first and/or second ion separation electrode assemblies) but also in a direction substantially parallel with the first and/or second ion separation electrode assemblies (or parallel with a tangent to the first and/or second ion separation electrode assemblies).

2.2. The apparatus of clause 2.1 wherein one of the first and second ion separation electrode assemblies is curved in the plane orthogonal to the direction of elongation of the channel.

2.3. The apparatus of clause 2.2 wherein both the first and second ion separation electrode assemblies are curved in the plane orthogonal to the direction of elongation of the channel.

2.4. The apparatus of clause 2.2 wherein one of the first and second ion separation electrode assemblies is curved in the plane orthogonal to the direction of elongation of the channel and the other of the first and second ion separation electrode assemblies is straight in the plane orthogonal to the direction of elongation of the channel.

2.5. The apparatus of any preceding clause wherein a cross sectional shape of the first and second ion separation electrode assemblies is constant for every plane orthogonal to the direction of elongation of the channel.

2.6. The apparatus of any preceding clause wherein the first ion separation electrode assembly comprises a plurality of electrode segments in the direction of elongation of the channel, each electrode segment being electrically isolated from adjacent electrode segments.

2.7. The apparatus of clause 2.6 wherein the plurality of electrode segments comprises a first subset of electrode segments and a second subset of electrode segments, and wherein the apparatus further comprises a controller arranged to apply a first separation voltage to the first subset of electrode segments of the first ion separation electrode assembly and arranged to apply a second separation voltage to the second ion separation electrode assembly, such that the first subset of electrode segments are at a different potential from the second subset of electrode segments.

2.8. The apparatus of clause 2.7 wherein the controller is further arranged to apply a third separation voltage to the second subset of electrode segments of the first ion separation electrode assembly.

2.9. The apparatus of clause 2.7 or clause 2.8 wherein the controller is arranged to apply a plurality of separation voltages to a plurality of subsets of electrode segments of the first ion separation electrode assembly.

2.10. The apparatus of any of clauses 2.7 to 2.9 wherein the controller is arranged to apply the first separation voltage to the first subset of electrode segments during a first time period and to apply the first separation voltage to the second subset of electrode segments during a second time period such that a field generated by the applied voltages in the first ion separation electrode assembly moves in the direction of elongation of the ion separation channel.

2.11. The apparatus of clause 2.10 wherein the controller is arranged to apply a plurality of separation voltages to a plurality of subsets of electrode segments of the first ion separation electrode assembly during a first time period and to shift the plurality of separation voltages along the subset of electrode segments during a second time period.

2.12. The apparatus of any preceding clause wherein the second ion separation electrode assembly comprises a plurality of electrode segments in the direction of elongation of the channel.

2.13. The apparatus of any preceding clause wherein one of the first and second ion separation electrode assemblies is helical.

2.14. The apparatus of any one or clauses 2.1 to 2.13 wherein one of the first and second ion separation electrode assemblies is conical.

2.15. A method for separating ions, the method comprising:

providing an elongate ion separation channel defined by a plurality of channel walls for constraining ions within the said channel, a first channel wall comprising a first ion separation electrode assembly and a second channel wall comprising a second ion separation electrode assembly wherein a length of the first ion separation electrode assembly and a length of the second ion separation electrode assembly each extend in a direction substantially parallel to the direction of elongation of the channel and a width of the first ion separation electrode assembly and a width of the second ion separation electrode assembly each extends in a plane orthogonal to the direction of elongation of the channel and wherein a distance separating the said first and second ion separation electrode assemblies varies along the width of the first and second ion separation electrode assemblies in that plane;

directing ions into the ion separation channel;

applying a first separation voltage to at least one of the first and second ion separation electrode assemblies in order to generate a periodically asymmetric electric field in the channel such that ions flow along the direction of elongation of the channel and are caused to separate in the direction of elongation according to differential ion mobility.

Advantageously, this provides an element of ion focusing in the said plane not only in a direction substantially perpendicular to the first and/or second ion separation electrode assemblies (or perpendicular to a tangent to the first and/or second ion separation electrode assemblies) but also in a direction substantially parallel with the first and/or second ion separation electrode assemblies (or parallel with a tangent to the first and/or second ion separation electrode assemblies).

2.16. The method of clause 2.15 wherein one of the first and second ion separation electrode assemblies is curved in the plane orthogonal to the direction of elongation of the channel.

2.17. The method of clause 2.16 wherein both the first and second ion separation electrode assemblies are curved in the plane orthogonal to the direction of elongation of the channel.

2.18. The method of clause 2.16 wherein one of the first and second ion separation electrode assemblies is curved in the plane orthogonal to the direction of elongation of the channel and the other of the first and second ion separation electrode assemblies is straight in the plane orthogonal to the direction of elongation of the channel.

2.19. The method of any of clauses 2.15 to 2.18 wherein a cross sectional shape of the first and second ion separation electrode assemblies is constant for every plane orthogonal to the direction of elongation of the channel.

2.20. The method of any of clauses 2.15 to 2.19 wherein the first ion separation electrode assembly comprises a plurality of electrode segments in the direction of elongation of the channel, each electrode segment being electrically isolated from adjacent electrode segments.

2.21. The method of clause 2.20 further comprising:

applying the first separation voltage to a first subset of the electrode segments of the first ion separation electrode assembly;

such that the first subset of the electrode segments are at a different potential from the second subset of electrode segments.

2.22. The method of clause 2.21 further comprising applying a second separation voltage to the second subset of electrode segments of the first ion separation electrode assembly.

2.23. The method of clause 2.21 further comprising applying a plurality of separation voltages respectively to a plurality of subsets of electrode segments of the first ion separation electrode assembly.

2.24. The method of clause 2.22 or clause 2.23 further comprising applying the first separation voltage of a plurality of separation voltages to the first subset of the electrode segments during a first time period and applying the first separation voltage of the plurality of separation voltages to the second subset of the electrode segments during a second time period such that a field generated by the applied voltages in the first ion separation electrode assembly moves in the direction of elongation of the ion separation channel.

2.25. The method of clause 2.24 comprising applying a plurality of separation voltages to a plurality of subsets of electrode segments of the first ion separation electrode assembly during a first time period and shifting the plurality of separation voltages along the subset of electrode segments during a second time period.

2.26. The method of any of clauses 2.21 to 2.25 wherein the ions are directed into the ion separation channel by entrainment in a carrier gas.

2.27. The method of clause 2.26 wherein a movement of the application of each of the plurality of separation voltages to the electrode segments is matched to a velocity of the carrier gas travelling through the ion separation channel.

3.1 An apparatus for separating ions comprising:

an elongate ion separation channel defined by a plurality of channel walls for constraining ions within the said channel, a first channel wall comprising a first ion separation electrode assembly and a second channel wall comprising a second ion separation electrode assembly and being spaced from the said first ion separation electrode assembly in a direction transverse to a direction of elongation of the channel, wherein the first ion separation electrode assembly comprises a plurality of electrode segments in the direction of elongation of the channel, each electrode segment being electrically isolated from adjacent electrode segments, the plurality of electrode segments comprising a first subset of electrode segments and a second subset of electrode segments; and a controller arranged to apply a first separation voltage to the first subset of the electrode segments of the first ion separation electrode assembly and arranged to apply a second separation voltage to the second ion separation electrode assembly such that the first subset of electrode segments is at a different potential from the second subset of electrode segments.

Advantageously, this allows for the field within the ion separation channel to be non-constant along its length which, in turn, allows for multiple ions to have stable trajectories.

3.2. The apparatus of clause 3.1 wherein the controller is further arranged to apply a third separation voltage to the second subset of electrode segments of the first ion separation electrode assembly.

3.3. The apparatus of clause 3.2 wherein the controller is arranged to apply a plurality of separation voltages to a plurality of subsets of electrode segments of the first ion separation electrode assembly.

3.4. The apparatus of clause 3.1 or clause 3.2 wherein the controller is arranged to apply the first separation voltage to the first subset of electrode segments during a first time period and to apply the first separation voltage to the second subset of electrode segments during a second time period such that a field generated by the applied voltages in the first ion separation electrode assembly moves in the direction of elongation of the ion separation channel.

3.5. The apparatus of clause 3.4 wherein the controller is arranged to apply a plurality of separation voltages to a plurality of subsets of electrode segments of the first ion separation electrode assembly during a first time period and to shift the plurality of separation voltages along the subsets of electrode segments during a second time period.

3.6. The apparatus of any of clauses 3.1 to 3.5 wherein the second ion separation electrode assembly comprises a plurality of electrode segments in the direction of elongation of the channel.

3.7. The apparatus of any of clauses 3.1 to 3.6 wherein one or both of the first and second ion separation electrode assemblies is cylindrical.

3.8. The apparatus of any one or clauses 3.1 to 3.6 wherein one or both of the first and second ion separation electrode assemblies is helical.

3.9. The apparatus of any of clauses 3.1 to 3.8 wherein the plurality of channel walls comprises a third channel wall which is substantially helical in shape.

3.10. The apparatus of any one or clauses 3.1 to 3.6 wherein one or both of the first and second ion separation electrode assemblies is conical.

3.11. The apparatus of any of clauses 3.1 to 3.10 wherein the first and second ion separation electrode assemblies are substantially coaxial and the first ion separation electrode assembly is arranged radially within the second ion separation electrode assembly.

3.12. The apparatus of any of clauses 3.1 to 3.10 wherein the first and second ion separation electrode assemblies are substantially coaxial and the second ion separation electrode assembly is arranged radially within the first ion separation electrode assembly.

3.13. The apparatus of clause 3.1 wherein the first ion separation electrode assembly has a first radius of curvature and the second ion separation electrode assembly has a second radius of curvature, wherein the first and second radii of curvature are different.

3.14. The apparatus of clause 3.13 wherein the radius of curvature of one of the first and second ion separation electrode assemblies is infinite.

3.15. The apparatus of clause 3.1 wherein the first ion separation electrode assembly is helical and the second ion separation electrode assembly is cylindrical.

3.16. A hybrid FAIMS-MS apparatus comprising the apparatus of any of clauses 3.1 to 3.15 and a source of ions.

3.17. A method for separating ions, the method comprising:

providing an elongate ion separation channel defined by a plurality of channel walls for constraining ions within the said channel, a first channel wall comprising a first ion separation electrode assembly and a second channel wall comprising a second ion separation electrode assembly and being spaced from the said first ion separation electrode assembly in a direction transverse to a direction of elongation of the channel, the first ion separation electrode assembly comprising a plurality of electrode segments in the direction of elongation of the channel, each electrode segment being electrically isolated from adjacent electrode segments, the plurality of electrode segments comprising a first subset of electrode segments and a second subset of electrode segments;

directing ions into the ion separation channel;

applying a first separation voltage to a first subset of the electrode segments of the first ion separation electrode assembly ion separation electrode assembly;

applying a second separation voltage to the second ion separation electrode assembly such that the first subset of the electrode segments is at a different potential from the second subset of electrode segments.

Advantageously, this allows for the field within the ion separation channel to be non-constant along its length which, in turn, allows for multiple ions to have stable trajectories.

3.18. The method of clause 3.17 further comprising applying a third separation voltage to the second subset of electrode segments of the first ion separation electrode assembly.

3.19. The method of clause 3.17 further comprising applying a plurality of separation voltages respectively to a plurality of subsets of electrode segments of the first ion separation electrode assembly.

3.20. The method of clause 3.18 or clause 3.19 further comprising applying the first separation voltage to the first subset of the electrode segments during a first time period and applying the first separation voltage to the second subset of the electrode segments during a second time period such that a field generated by the applied voltages in the first ion separation electrode assembly moves in the direction of elongation of the ion separation channel.

3.21. The method of clause 3.20 comprising applying a plurality of separation voltages to a plurality of subsets of electrode segments of the first ion separation electrode assembly during a first time period and shifting the plurality of separation voltages along the subset of electrode segments during a second time period.

3.22. The method of any of clauses 3.17 to 3.21 wherein the ions are directed into the ion separation channel by entrainment in a carrier gas.

3.23. The method of clause 3.22 wherein a movement of the application of each of the plurality of separation voltages to the electrode segments is matched to a velocity of the carrier gas travelling through the ion separation channel.

4.1. A high-field asymmetric waveform ion mobility separation apparatus comprising:

an elongate ion separation channel defined by a plurality of channel walls for constraining ions within the said channel, wherein the channel walls comprise:

first and second generally opposed ion separation electrode assemblies, each extending in one or more separation planes; and first and second generally opposed ion focusing electrode assemblies, each extending in one or more focusing planes different from the separation planes, such that the ion separation channel is generally bounded or enclosed by the first and second ion separation electrode assemblies and the first and second ion focusing electrode assemblies, the apparatus further comprising a power supply for applying a periodic asymmetric potential to at least one of the first and second ion separation electrode assemblies in order to generate a periodically asymmetric electric field in the channel such that ions which flow along the direction of elongation of the channel are caused to separate according to differential ion mobility.

Advantageously, this allows for different separation voltages to be applied to: the first ion separation electrode assembly; the second ion separation electrode assembly; the first ion focusing electrode assembly; and the second ion focusing electrode assembly, in order to provide increased focusing of the ions flowing within the ion separation channel. Increased focusing allows for a longer separation channel which allows for increased sensitivity.

4.2. The apparatus of clause 4.1 wherein:

the first ion separation electrode assembly is a first, inner cylindrical electrode and the second ion separation electrode assembly is a second, outer cylindrical electrode arranged substantially coaxially with the said first ion separation electrode assembly; and the first and second ion focusing electrode assemblies are each plate-like electrodes and wherein the plane of each electrode extends in a direction generally orthogonal to the coaxis of the cylindrical electrodes.

4.3. The apparatus of clause 4.1 wherein:

the first ion focusing electrode assembly is a first, inner cylindrical electrode and the second focusing separation electrode assembly is a second, outer cylindrical electrode arranged substantially coaxially with the said first ion focusing electrode assembly; and the first and second ion separation electrode assemblies are each plate-like electrodes and wherein the plane of each electrode extends in a direction generally orthogonal to the coaxis of the cylindrical electrodes.

4.4. The apparatus of clause 4.2 or clause 4.3 wherein the plate-like electrodes are annular.

4.5. The apparatus of any of clauses 4.2 to 4.4 wherein the plate-like electrodes are strictly orthogonal to the coaxis of the cylindrical electrodes.

4.6. The apparatus of any of clauses 4.2 to 4.5 wherein the plate-like electrodes are arranged to act as Matsuda plates.

SPECIFIC DESCRIPTION

Preferred embodiments of the invention will now be described, by way of example only, with reference to the accompanying drawings in which:

FIG. 5D shows a perspective view of an improved FAIMS device with a cutaway portion, the device having a helical shaped ion focusing electrode assembly (visible through the cutaway portion) within the annular gap between two coaxial cylindrical ion separation electrode assemblies;

FIG. 5E shows a cutaway side view of the improved FAIMS device of FIG. 5D, with the helical shaped ion focusing electrode not shown;

FIG. 5F shows a portion of the helical shaped ion focusing electrode of the FAIMS device illustrated in FIGS. 5D and 5E;

Figure 1A:
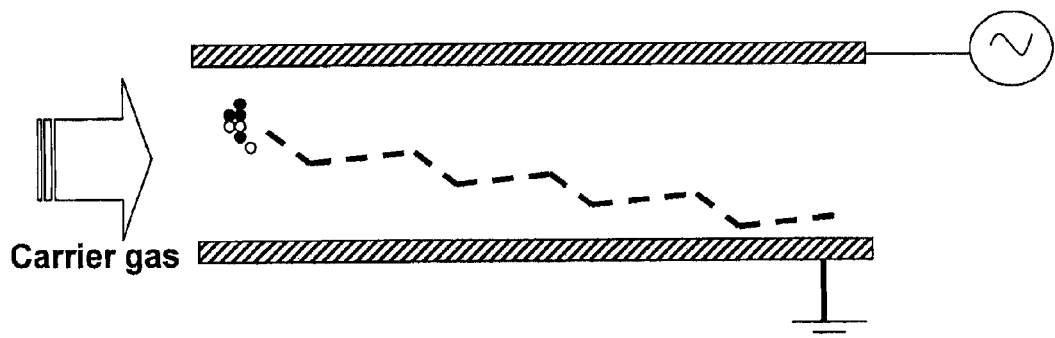
FIG. 1A shows a prior art FAIMS device having two flat parallel plate electrodes providing a straight ion path.
Figure 1B:
FIG. 1B shows a typical FAIMS voltage distribution plot showing short periods of high voltage and longer periods of lower voltage of opposite polarity.

The improved FAIMS of FIGS. 4A to 4D is a side to side arrangement having an inner cylindrical ion separation electrode 50, an outer cylindrical ion separation electrode 70, with slits 75a, 75b for the entry and exit of ions, and annular electrodes 60 above and below the intended ion path. The ion path is indicated by the arrows shown in FIGS. 4B and 4C. For clarity, FIG. 4A to 4D show only the electrodes, but in practice insulating components are placed between the electrodes by which the channel can be made contiguous.

In use, ions to be separated are entrained in a gas flow (from a gas flow source, not shown) which enters the FAIMS device at a first open end 75a of the channel defined by the two ion separation electrodes 50, 70 and the annular ion focusing electrodes 60. A power supply (not shown) applies a periodic asymmetric potential to at least one of the ion separation electrode assemblies 50, 70 in order to generate a periodically asymmetric electric field in the annular channel such that ions flow along the direction of elongation of the channel and are caused to separate according to differential ion mobility. A DC offset voltage or compensation voltage (CV) is typically applied to one of the ion separation electrode assemblies 50, 70 to select the ions to be transmitted through the annular channel. This causes ions to separate in a direction orthogonal to the direction of flow of the gas (i.e. the direction orthogonal to the direction of elongation of the channel). The separated ions are then exit the FAIMS device at the second open end 75b.

The annular ion focusing electrodes 60 may be configured to act as Matsuda plates. This allows for the disadvantages associated with having a channel of largely square or rectangular cross-section to be minimised. It is known that aberrations in a channel are reduced by having a channel with a toroidal cross-section. By using Matsuda plates, a field similar to that which would be created in a channel with toroidal cross-section is created in a channel with square or rectangular cross-section by the interaction of the field generated by the ion separation electrode assemblies 50, 70 and the field generated by the ion focusing electrode assemblies 60. (A further explanation of Matsuda plates is provided by H. Matsuda and Y. Fujita; "Potential Distribution In A Cylindrical Condenser Terminated By Matsuda Plates"; International Journal of Mass Spectrometry and Ion Physics, 16 (1975) 395-404.)

Figure 5A:
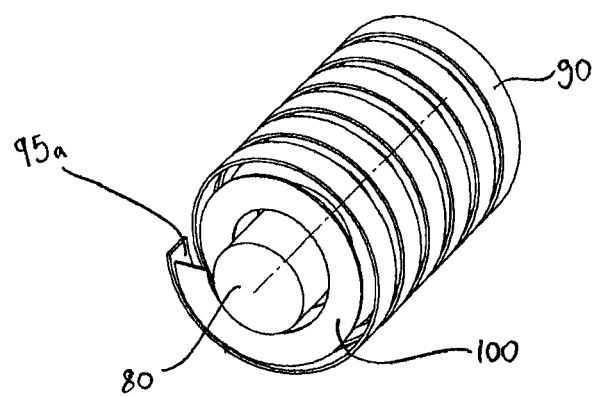
FIG. 5A shows a perspective view of an improved FAIMS device having a helical shaped ion separation electrode assembly interleaved with a helical shaped ion focusing electrode assembly.

FIG. 5A shows another improved FAIMS electrode arrangement. It comprises a central cylindrical ion separation electrode 80 and a coaxial outer helical shaped separation electrode 90. It also comprises a helical ion focusing electrode 100, which may be configured to act as a Matsuda plate. These electrode assemblies together define a helical ion separation channel. For clarity, FIG. 5A shows only the electrodes, but in practice insulating components are placed between the electrodes by which the channel can be made contiguous. Having a helical channel provides for an increased length of ion flow path while maintaining the curvature of the inner and outer electrodes.

In use, ions to be separated are entrained in a gas flow (from a gas flow source, not shown) which enters the FAIMS device at a first open end 95a of the helical channel defined by the two ion separation electrodes and the helical ion focusing electrode. The helical channel is preferably substantially gastight so that the ions are carried in the gas flow along the length of the channel. A power supply (not shown) applies a periodic asymmetric potential to at least one of the ion separation electrode assemblies 80, 90 in order to generate a periodically asymmetric electric field in the helical channel such that ions flow along the direction of elongation of the channel and are caused to separate according to differential ion mobility. A DC offset voltage or compensation voltage (CV) is typically applied to one of the ion separation electrode assemblies 80, 90 to select the ions to be transmitted through the helical channel.

As the ions flow through the helical channel, the helical ion separation electrode 90 and the internal cylindrical ion separation electrode 80 offer the focusing in the radial direction while the helical focusing electrode 100 offers focusing in the axial direction. The gas flow which includes the ions, which are separated in a direction orthogonal to the elongate direction of the channel (i.e. orthogonal to the direction of flow of the gas), exits the arrangement from a second open end 95b of the helical cavity, which is opposite the first open end 95a of the helical cavity.

Advantageously, when different values of DV and/or CV from those applied to the ion separation electrode assemblies are applied to the ion focusing electrode, the field produced provides focusing in the axial direction (i.e. the direction of net movement of ions) as well as in the circumferential direction.

Figure 4:
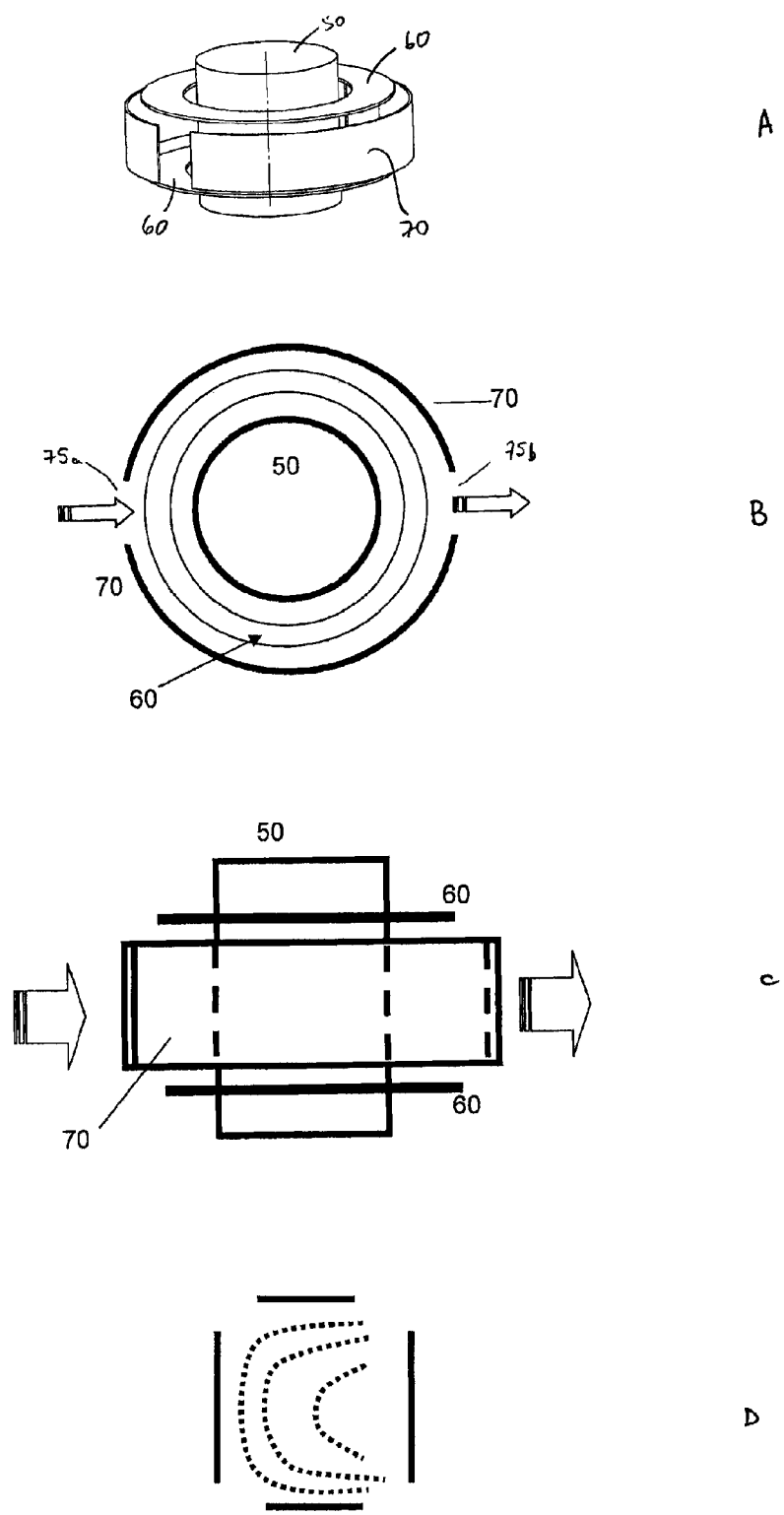
FIG. 4A shows a perspective view of an improved FAIMS device wherein above and below the ion path of a side-to-side FAIMS device are annular electrodes.
FIG. 4B shows the improved FAIMS device of FIG. 4A when viewed from above.
FIG. 4C shows the improved FAIMS device of FIG. 4A when viewed from the side.
FIG. 4D shows the field formed by the FAIMS device of FIGS. 4A, 4B and 4C.

The helical cavity provides a significantly increased path length as compared with the side-to-side apparatus illustrated in FIG. 4. This results in greater separation between different species of ions which significantly improves the sensitivity of the device.

Further alternative embodiments having a helical ion separation channel are envisaged. It is not necessary that one (or both) of the ion separation electrode assemblies is helical, only that the ion separation channel is helical.

Figure 5B:
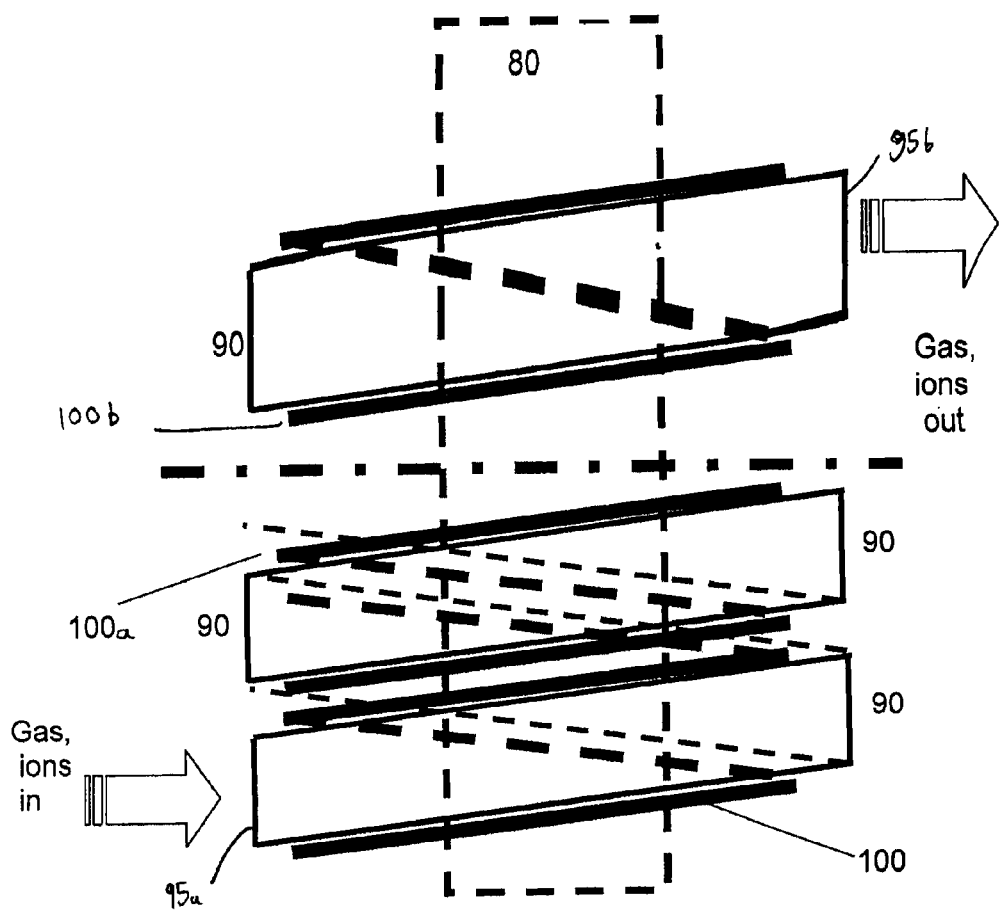
FIG. 5B shows a side view of an improved FAIMS device having a helical shaped ion separation electrode assembly interleaved with a helical shaped ion focusing electrode assembly, the helical shaped ion focusing electrode assembly comprising two helical shaped electrodes.
Figure 5C:
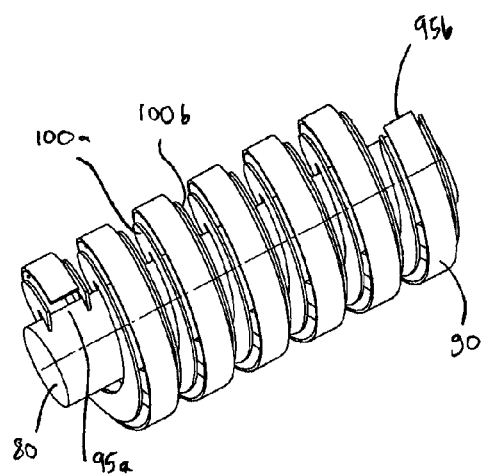
FIG. 5C shows a perspective view of the improved FAIMS device of FIG. 5B.

FIGS. 5B and 5C show a variation of the embodiment of FIG. 5A. The arrangement of FIGS. 5B and 5C includes two helical ion focusing electrodes 100a, 100b which are both interleaved between the helical ion separation electrode 90, one being below the ion separation electrode 90, and one above it. In this arrangement, the cavity through which the gas and ions flow is defined by the two ion separation electrodes and the two helical ion focusing electrodes. Again, for clarity, FIGS. 5B and 5C show only the electrodes, but in practice insulating components are placed between the electrodes by which the channel can be made contiguous.

Alternatively, the helical ion separation channel may be achieved where neither of the ion separation electrodes is helical. Such an embodiment is illustrated in FIGS. 5D to 5F.

In this embodiment, the helical ion separation channel is formed of two coaxial cylindrical ion separation electrode assemblies and a single helical ion focusing electrode assembly in the annular gap between the two coaxial ion separation electrode assemblies. The helical ion separation electrode assembly may comprise a number of component parts of the form illustrated in FIG. 5F such that the helical nature of the assembly is derived from the combination of component parts. These component parts may be fastened to one or both of the ion separation electrode assemblies by means of one or more grub screws (101). Further, the outer cylindrical ion separation electrode assembly may comprise a groove on its inner surface and the inner cylindrical ion separation electrode assembly may comprise a corresponding groove on its outer surface such that a helical ion focusing electrode assembly is positioned in the two grooves. This requires some form of insulation in order to prevent current flow between the electrodes. The insulation between the electrodes might be achieved by forming the helical electrode from an electrically conductive material with insulated edges such that only the insulated edges are received into the helical grooves in the electron separation electrodes. Alternatively, the electrodes may be made from an insulating material (substrate) with a metal coating applied to part of its surface. Other arrangements are envisaged so long as the ion focusing and ion separation electrodes are not in electrical contact with one another. Anti-static coatings may be applied to any insulating portions in order to dissipate charge.

It is also possible that both the first ion separation electrode assembly and the second ion separation electrode are helical. (Such an embodiment is not illustrated.) Where only one of the ion separation electrode assemblies is helical, the other may be cylindrical, conical, frustoconical or any other suitable shape in order to form a helical channel. Where only one ion separation electrode assembly is helical, it may be the outer or the inner ion separation electrode assembly.

In further alternatives, the first and second ion separation electrode assemblies may be conical, frustoconical or any other shape suitable such that, when combined with one or more helical ion focusing electrodes, the ion separation channel is helical. Where one or more helical electrodes are used, one or both may be of constant or varying radius.

Furthermore, while the embodiments illustrated in the Figures show that the side walls of the channel form a square section, this is not a requirement of the invention. Other straight or curved sections are possible, including but not limited to a rectangle, a rhombus, a trapezium, a circle, an oval, or more irregular shapes. The ion focusing electrode assembly may, for example, have a curved cross section such that the ion separation channel is of a partially toroidal shape.

Similarly, it is not necessary that the cross section of the channel is constant along its length.

The ion separation electrode assembly and the ion focusing assembly may be reversed. That is, the ion focusing electrode assembly may be arranged in the generally axial direction while the ion separation assembly may be arranged generally in the circumferential direction. In practice insulating components are placed between the electrodes by which the channel can be made contiguous.

In respect of all of the helical channel arrangements illustrated in FIGS. 5A to 5F, for any plane orthogonal to the direction of elongation of the channel, the ion separation electrodes have a width which exists substantially in said plane and the ion focusing electrode(s) have a width which exists substantially in said plane. Moreover, each electrode has only two of its three dimensions (width and thickness) in the plane. The third dimension of each electrode (length) is substantially parallel with the direction of elongation of the channel and, therefore, not in the plane orthogonal to the direction of elongation.

Put another way, the ion separation electrode assemblies have a width which extends in a first direction in a plane orthogonal to the direction of flow of ions; and the ion focusing electrode assembly has a width which extends in a second direction in said plane. The first direction and the second direction may or may not be substantially perpendicular.

Figure 6A:
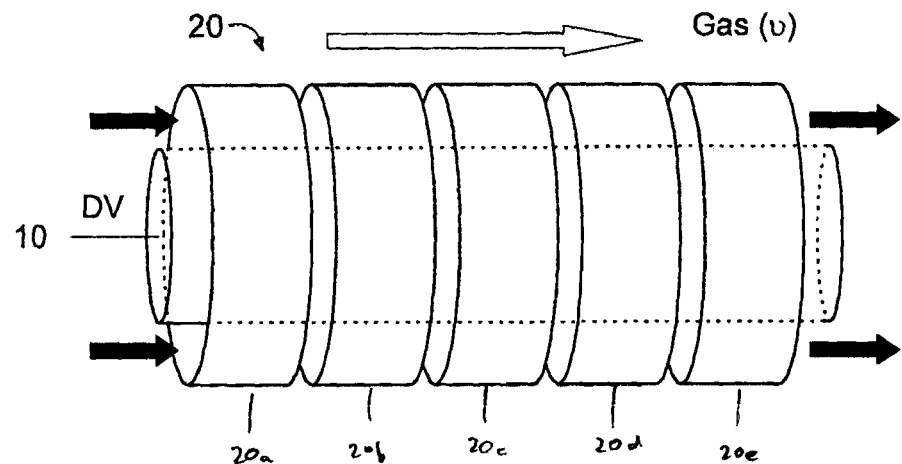
FIG. 6A shows an improved FAIMS device having an outer electrode which is divided into a plurality of segments.

FIG. 6A shows a segmented cylindrical FAIMS. This device comprises a cylindrical inner electrode 10 and a coaxial segmented cylindrical outer electrode 20 having segments 20a, 20b, 20c, 20d, 20e. Each of the segments 20a, 20b, 20c, 20d, 20e of the outer electrode 20 is electrically isolated from the adjacent segments. Thus, each segment of the outer electrode 20 can be placed at a different separation voltage from its adjacent segments.

The segmented cylindrical electrode may be formed from a plurality of discrete segments or as a single cylinder with insulating portions between each adjacent segment. In a further alternative, the cylinder may be formed from an insulating substrate with surface coatings of electrically conductive material applied to the cylinder to form each segment. Antistatic coatings may be applied to insulating portions. The antistatic coating has a resistance of the order of $10^6$ ohms per square (M$\Omega\square^{-1}$) to $10^9$ ohms per square (G$\Omega\square^{-1}$).

While five segments are shown in this illustration, any number of segments is envisaged (not only in this embodiment, but with any of the embodiments comprising a segmented electrode).

In use, a first separation voltage is applied to the inner (non-segmented) electrode 10. A second separation voltage is applied to at least one of the segments 20a, 20b, 20c, 20d, 20e of the outer electrode 20.

In one arrangement, the first separation voltage is a compensation voltage and the second separation voltage is a dispersion voltage. In an alternative arrangement, the first separation voltage is a dispersion voltage and the second separation voltage is a compensation voltage.

Third and subsequent separation voltages may be applied to others of the segments 20a, 20b, 20c, 20d, 20e. If the second separation voltage is a compensation voltage the third (and any subsequent) separation voltage will also be a (different) compensation voltage. If, on the other hand, the second separation voltage is a dispersion voltage then the third (and any subsequent) separation voltage will also be a (different) dispersion voltage.

By altering the separation voltage of each segment in turn, the potential values can be made to shift along the segments. This in turn generates a moving field which provides additional focusing of the ions as well as improving ion throughput as described below.

The electrode segments may be grouped together as subsets of the segments. For example, two adjacent electrode segments may be placed at the same voltage (during one particular, or more than one, time period) forming a subset of the totality of electrode segments. Alternatively, each electrode segment may be placed at a different voltage for a certain period meaning that during that period the number of subsets of electrode segments is equal to the total number of electrode segments.

Of course, it may be that the inner electrode is segmented instead of the outer electrode or that both the inner and the outer electrodes are segmented.

Figure 6B:
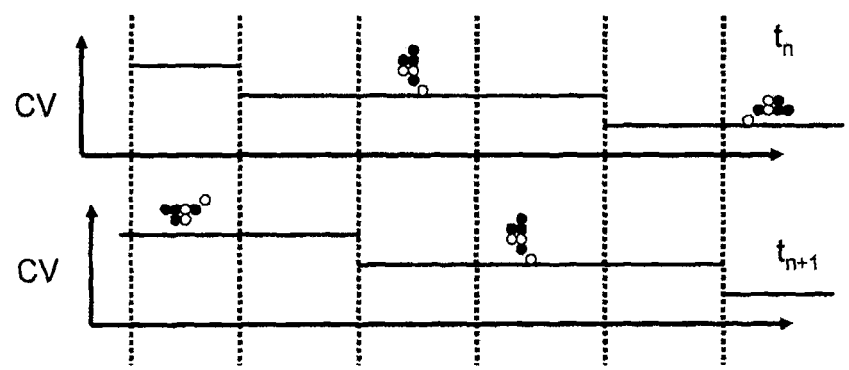
FIG. 6B shows a typical voltage distribution across the successive segments of the FAIMS device of FIG. 6A.

FIG. 6B shows how an example of the potential (CV) of each segment at a time $t_n$ and at subsequent time $t_{n+1}$. This illustrates how the potential appears to have shifted along by one segment.

In known FAIMS apparatus, a constant CV is required while the ions of interest are inside the FAIMS apparatus until they have been separated from the other ions and emerge from the apparatus. Then the next CV value may be applied to select the next ions of interest and so on. In other words a single CV value is applied for the whole time that the ions of interest are in the FAIMS apparatus. Longer times of analysis are required for higher peak separation capacity. Although the ions of interest should experience the same CV throughout the analysis, the area in space that a packet of ions occupies is limited. Consequently, segmented electrodes e.g. either the outer 20 or inner 10 electrodes, can be provided with a time dependent application of CV and/or DV (i.e. a CV and/or DV waveform), which can provide that multiple ions of interest can have stable trajectories at the same time. In other words two or more values of CV and/or DV are present among the set of segments at any one time in the separation of ions, i.e. different CV values are applied to different sets of segments. Preferably, a time dependent CV is applied. The regions where each CV and/or DV value is applied are spaced apart at a distance equal to the width in space of the CV and/or DV waveforms (as shown in FIG. 6B). The timing of the change of value on each segment needs to be matched with the velocity of the carrier gas. In this way the throughput of selected ions is significantly improved compared to conventional FAIMS apparatus.

Figure 7A:
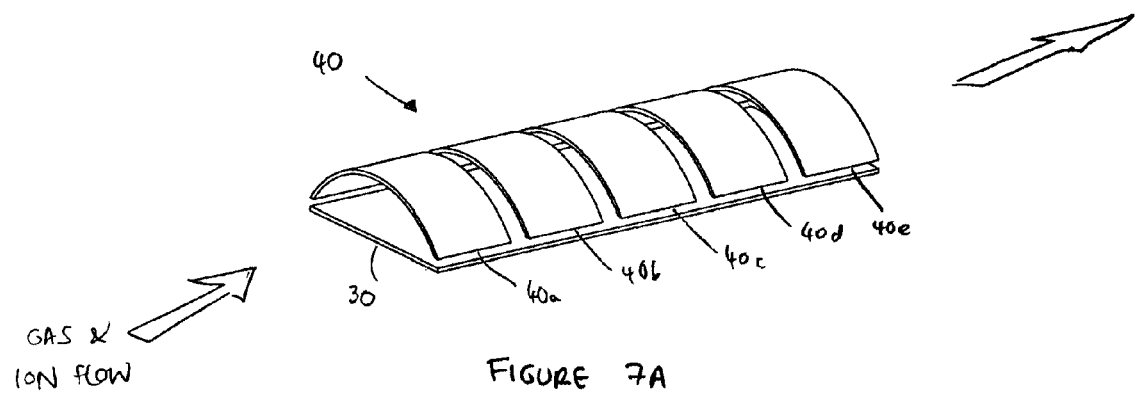
FIG. 7A shows a perspective view of an improved FAIMS device comprising two ion separation electrode assemblies each electrode assembly having a different radius of curvature, with one electrode assembly being segmented.
Figure 7B:
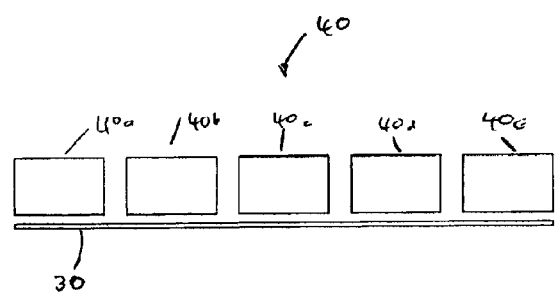
FIG. 7B shows a side view of the improved FAIMS of FIG. 7A.

FIGS. 7A and 7B shows a further example of an improved FAIMS device. In this example, the ions flow in the direction indicated by the arrows between a first electrode 30 and a second, segmented electrode 40 having a different radius of curvature from the first electrode 30. The electrodes 30 and 40 have the usual FAIMS separation voltages applied (as described above) to effect ion separation according to differential ion mobility. While FIG. 7A shows one of the two electrodes being planar (i.e. infinite radius of curvature), this is not essential. It is required only to have a different radius of curvature to the other electrode. It is also possible that the radius of curvature of one or both electrodes may change along the width of the electrode(s).

This arrangement provides for improved focusing in the radial direction by comparison, for example, with that provided by two planar parallel plates (such as those shown in FIG. 1A). By improving the focusing in this way, sensitivity of the device is also improved.

Figure 7C:
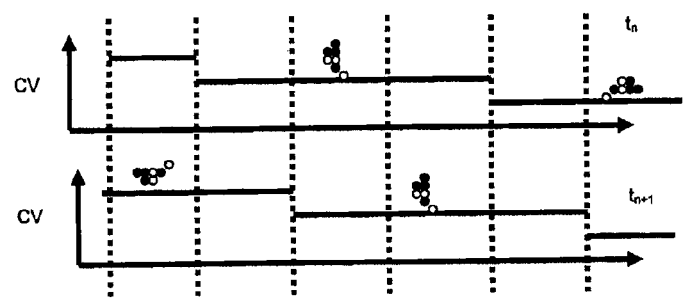
FIG. 7C shows a typical voltage distribution across the successive segments of the FAIMS device of FIGS. 7A and 7B.

As shown in FIG. 7C, the potential of the segmented electrode 40 may be shifted along, segment by segment, in the same way and for the same reasons as outlined above in respect of the FIG. 6A/6B embodiment.

Figure 2A:
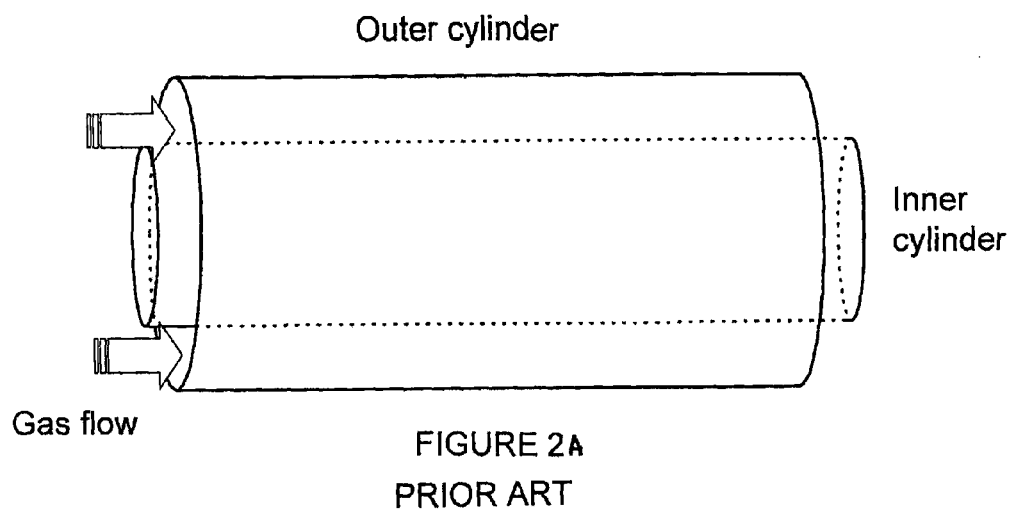
FIG. 2A shows a prior art cylindrical FAIMS device having a cylindrical capacitor.
Figure 2B:
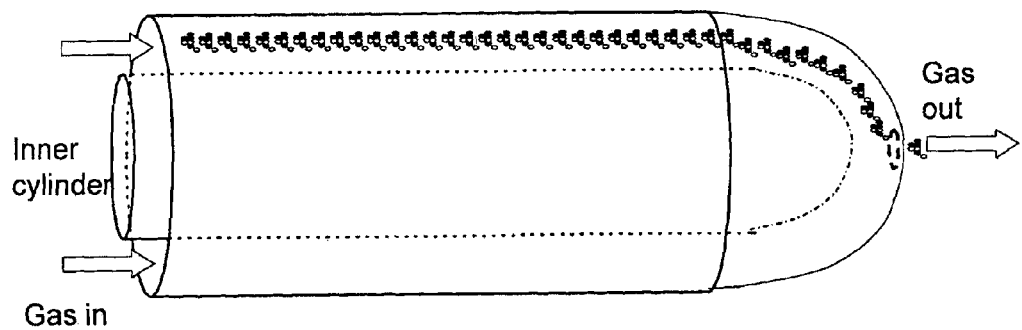
FIG. 2B shows a prior art dome-shaped FAIMS device.
Figure 3A:
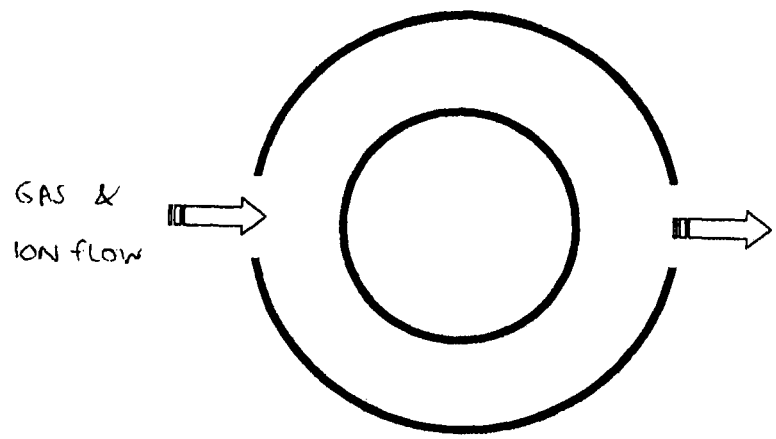
FIG. 3A shows a prior art side-to-side FAIMS device from above.
Figure 3B:
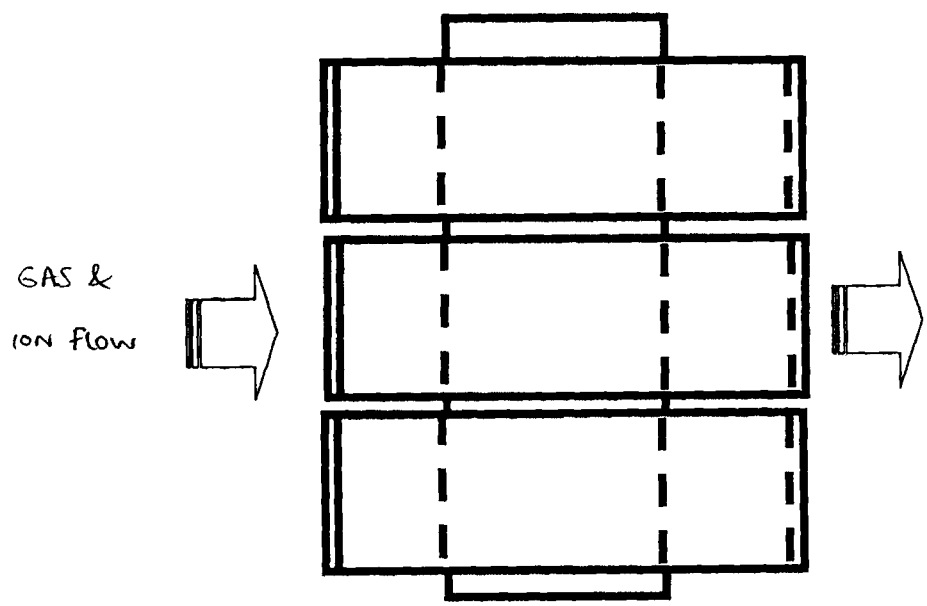
FIG. 3B shows the prior art side-to-side FAIMS device of FIG. 3A from the side, and illustrates an embodiment which includes segmentation of the outer electrode.

An alternative embodiment to that illustrated in FIG. 7 is one with two electrodes, each with a different radius of curvature, wherein neither electrode is segmented. Even without segmentation, this reduces loss of ions in the orthogonal direction (and hence improved focusing) by comparison with devices having an annular ion separation region, such as that illustrated in FIG. 2A.

Figure 8:
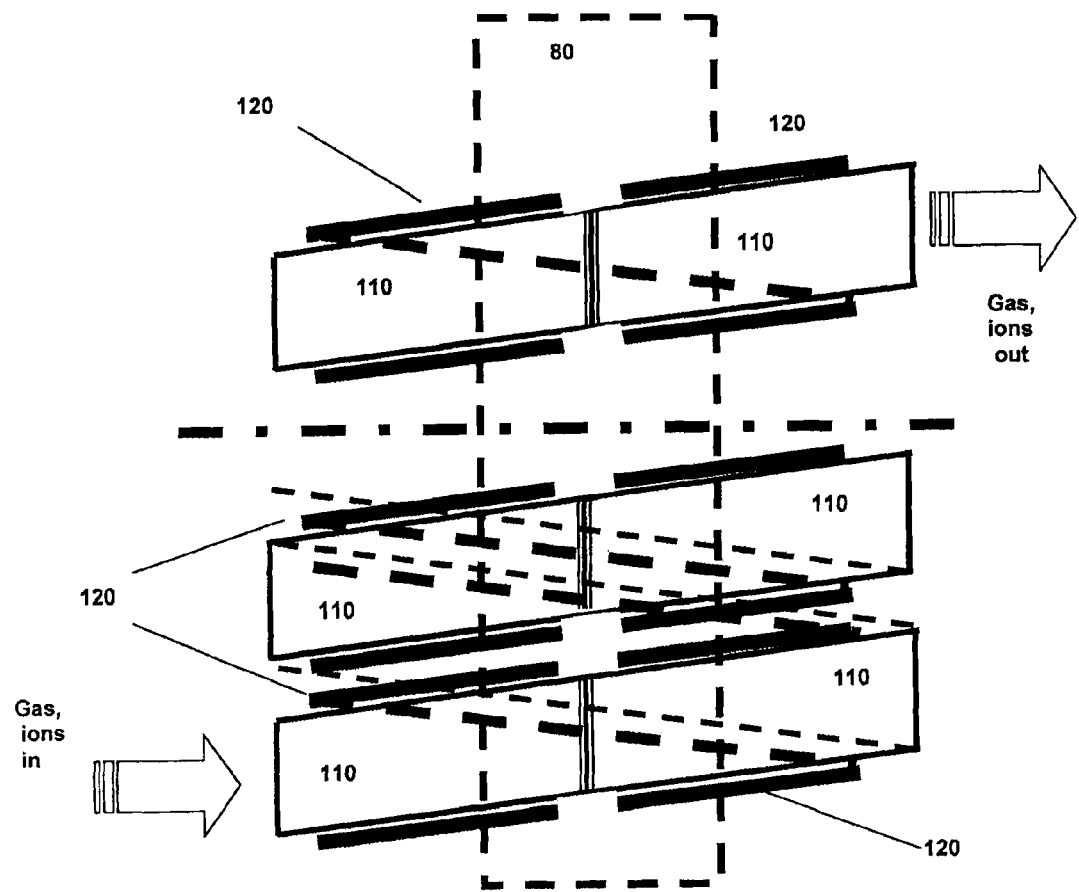
FIG. 8 shows an improved FAIMS device having a segmented helical shaped ion separation electrode assembly interleaved with two helical shaped ion focusing electrode assemblies.

The embodiment of FIG. 8 represents a modification of the FIG. 5 embodiments and comprises a cylindrical inner ion separation electrode 80, a segmented helical outer ion separation electrode 110, and a pair of segmented helical ion focusing electrodes 120. The segmented ion separation electrode may have the timed CV and/or DV applied as described above. This embodiment brings together the advantages of several of the embodiments already discussed. In particular, it combines the increased path length provided by the helical flow path with electrode segments which allow for the application of timed CV and/or DV changes. This provides the simultaneous advantages of longer residence times ($t_{res}$) without loss in sensitivity (therefore improved resolution) and an increase in duty-cycle by transporting ions selected by different CV values simultaneously.

Figure 9:
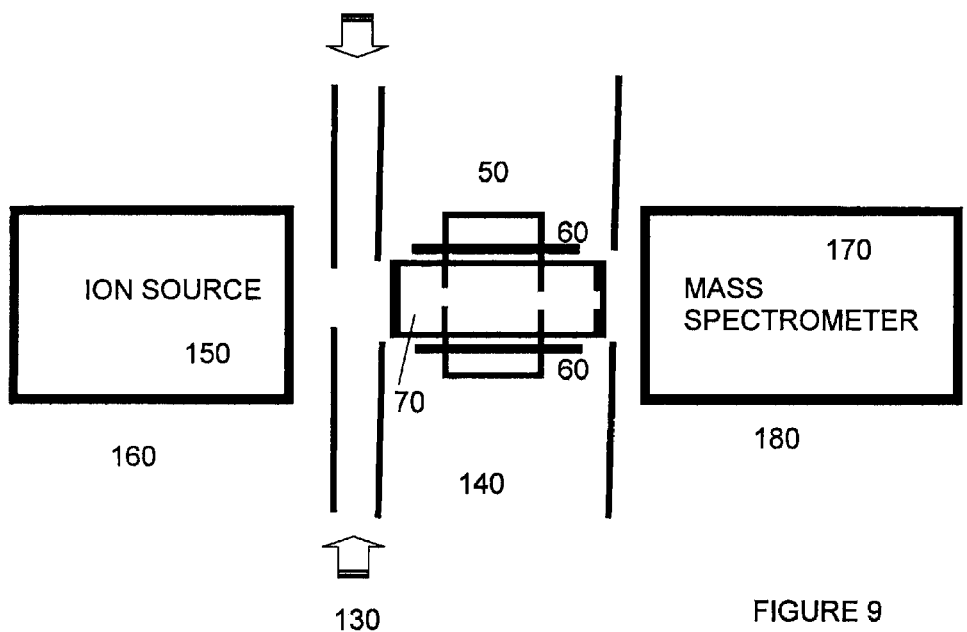
FIG. 9 shows a hybrid FAIMS-MS apparatus comprising the improved FAIMS of FIGS. 4A to 4D in use with an ion source, gas flow input path and mass spectrometer.

FIG. 9 provides a schematic representation of the FAIMS electrode arrangement of FIG. 4 together with an ion source 150 (e.g. ESI, APCI, MALDI, etc.), gas flow source 130 and mass spectrometer 170, all of which together make up hybrid a FAIMS-MS apparatus.

Figure 10:
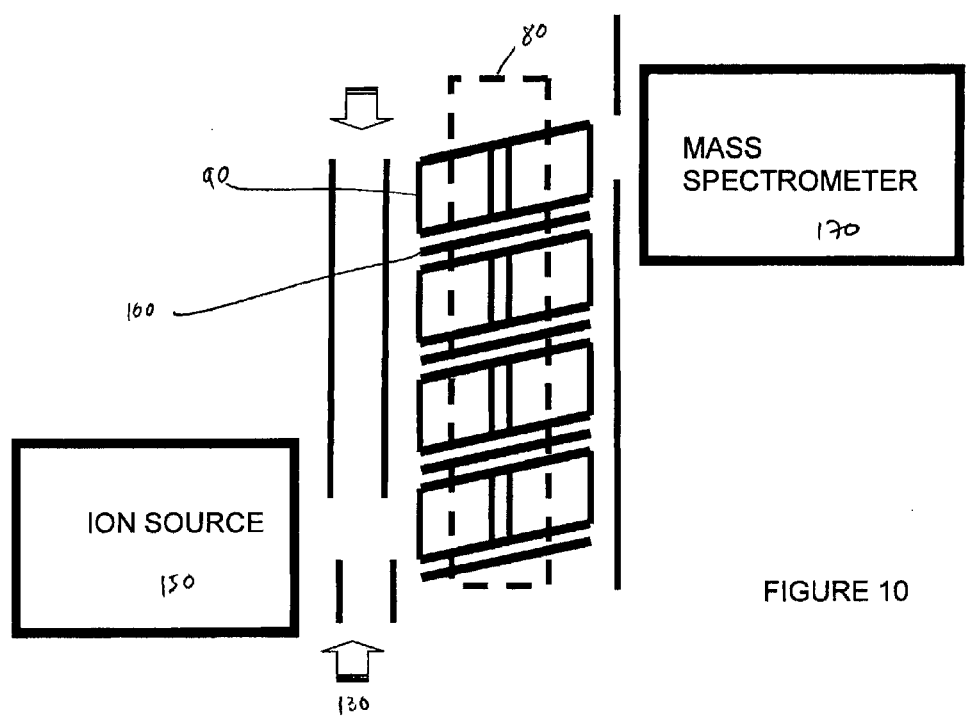
FIG. 10 shows a hybrid FAIMS-MS apparatus comprising the improved FAIMS of FIG. 5A in use with an ion source, gas flow input path and mass spectrometer.

FIG. 10 shows the FAIMS electrode arrangement of FIG. 5 together with an ion source 150, gas flow source 130 and mass spectrometer 170, all of which together make up a hybrid FAIMS-MS apparatus.

FIG. 10 differs from FIG. 9 largely in that the ion source 150 is axially offset from the mass spectrometer 180 as a consequence of the helical ion path giving rise to a net movement of ions in the axial direction of the helix. By contrast, the largely planar movement of ions in the FIG. 9 FAIMS electrode arrangement means that the ion source and mass spectrometer need not be offset.

Thus, FIGS. 9 and 10 are examples of two different arrangements of FAIMS device dependent on whether or not the ions in the FAIMS have a net axial movement. They are merely illustrative of the way in which any of the FAIMS electrode arrangements disclosed herein may be employed in a FAIMS apparatus. In general, any of the FAIMS electrode arrangements herein may be employed in a hybrid FAIMS-MS apparatus having ion source and mass spectrometer.

Any of the improved FAIMS apparatus disclosed above may be used in the context of multiple ion sources and either single or multiple FAIMS channels.

Figure 11:
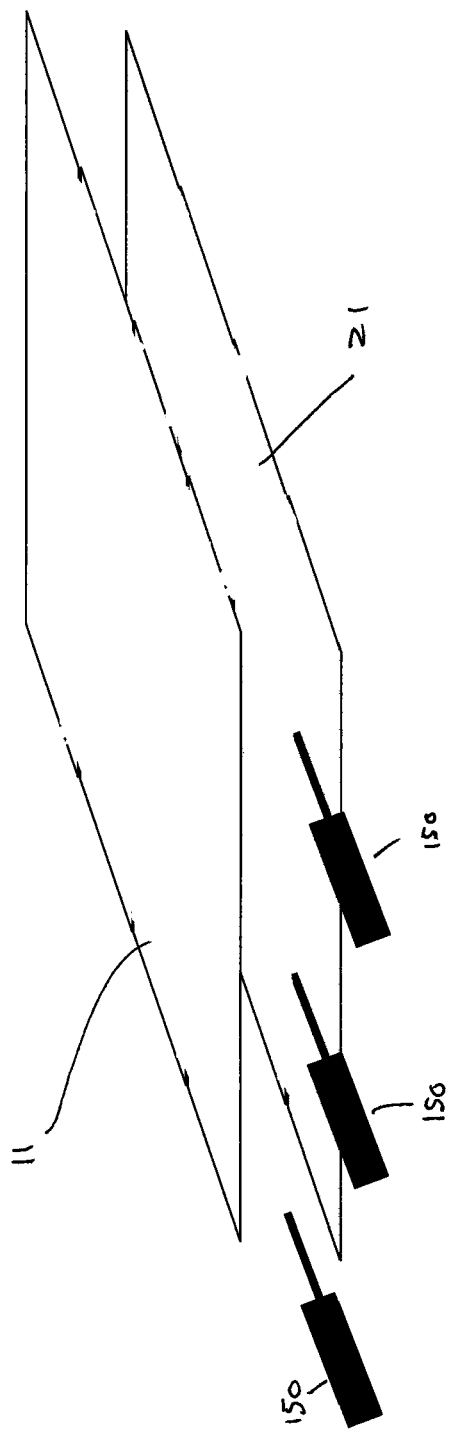
FIG. 11 shows a planar FAIMS device having multiple ion sources.

FIG. 11 illustrates a known planar FAIMS device having a plurality of electrospray ionisation (ESI) needles 150 each providing a source of ions to the FAIMS apparatus. The ESI needles may have microfabricated tips. The FAIMS device comprise a first electrode 11 and a second electrode 21.

Figure 12:
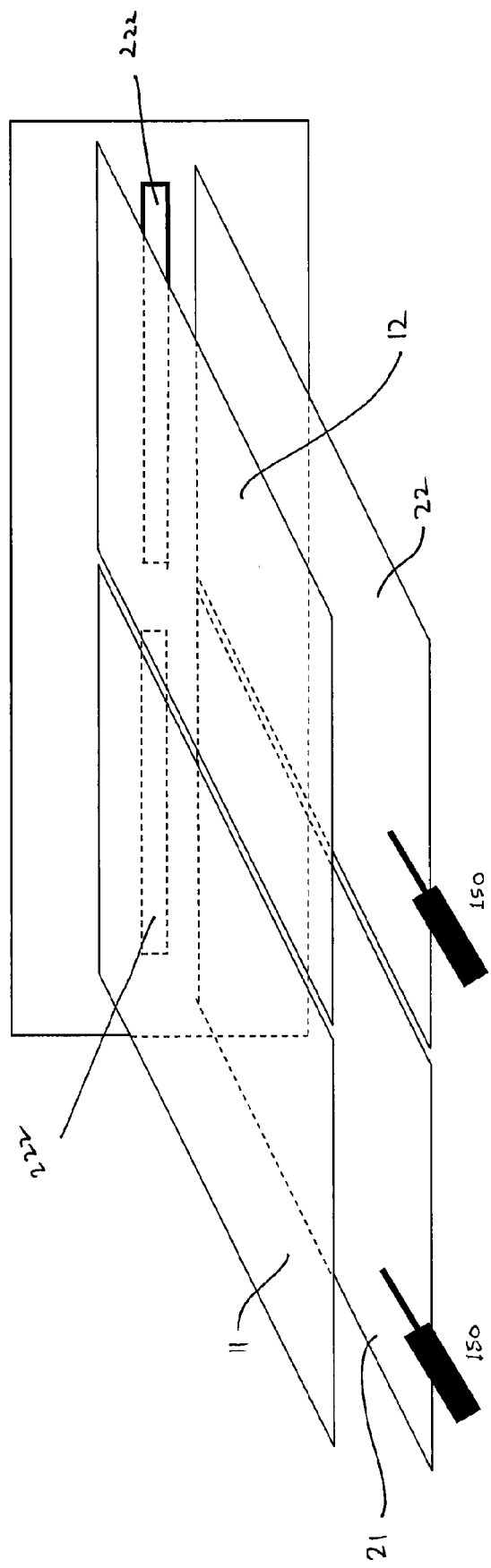
FIG. 12 shows two adjacent FAIMS devices each with its own ion source.

FIG. 12 shows two adjacent planar FAIMS channels each having its own ion source 150 wherein the values of compensation and/or dispersion voltage may be independently controlled for each channel. A first channel has first electrode 11 and second electrode 12 while a second channel has first electrode 21 and second electrode 22. At the exit of each of the FAIMS channels is a slot 222 through which ions exit the FAIMS channel. The slot might equally be replaced by a hole, capillary or other opening. Behind the said opening 222 there might be a stacked ring ion guide (SRIG) or an ion funnel.

Figure 13:
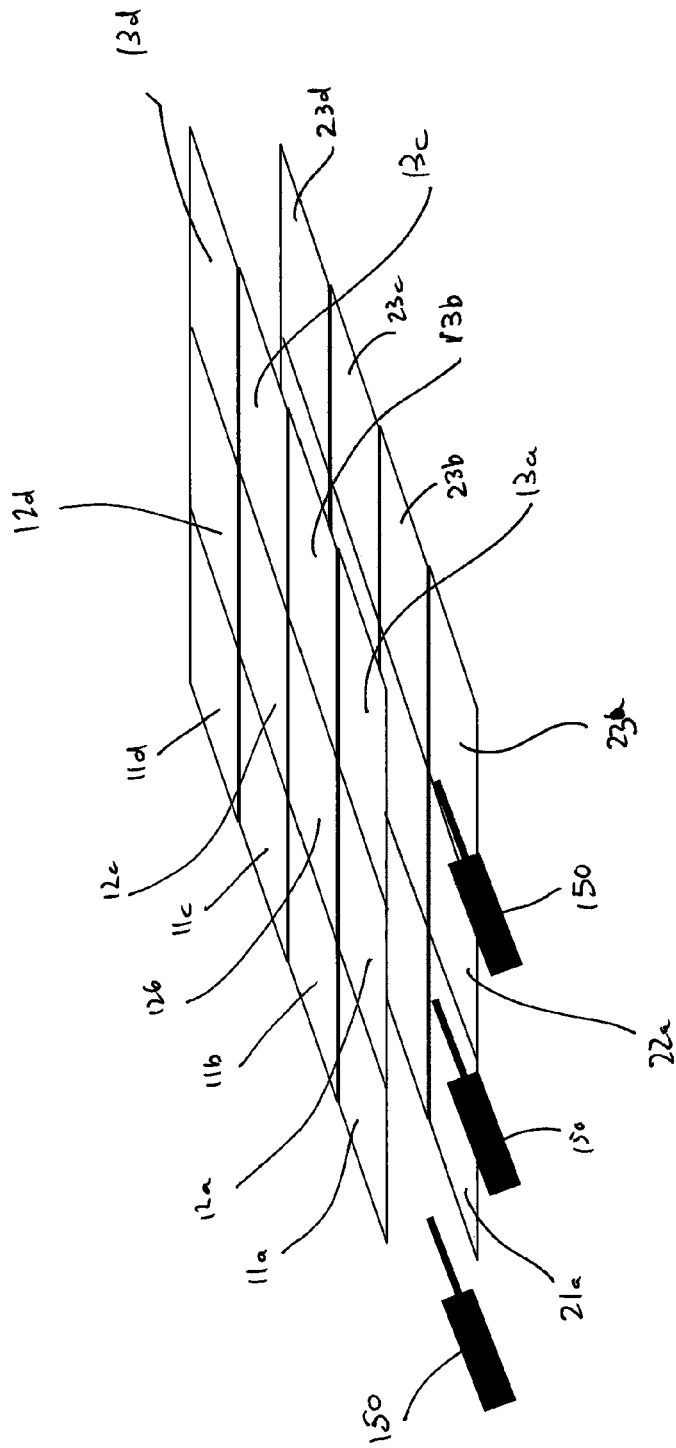
FIG. 13 shows three adjacent FAIMS devices each with its own ion source.

FIG. 13 shows a variation on the device of FIG. 12 but having three FAIMS channels and three ion sources. The FAIMS channels of FIG. 13 have segmented electrodes. The segmented electrodes (which, in the case of the first FAIMS channel are labelled 11a, 11b, 11c, 11d and 21a, 21b, 21c and 21d). The segmented electrodes gives rise to the advantages described above in respect of the segmented FAIMS devices of various geometries but having only a single ion source.

Figure 14:
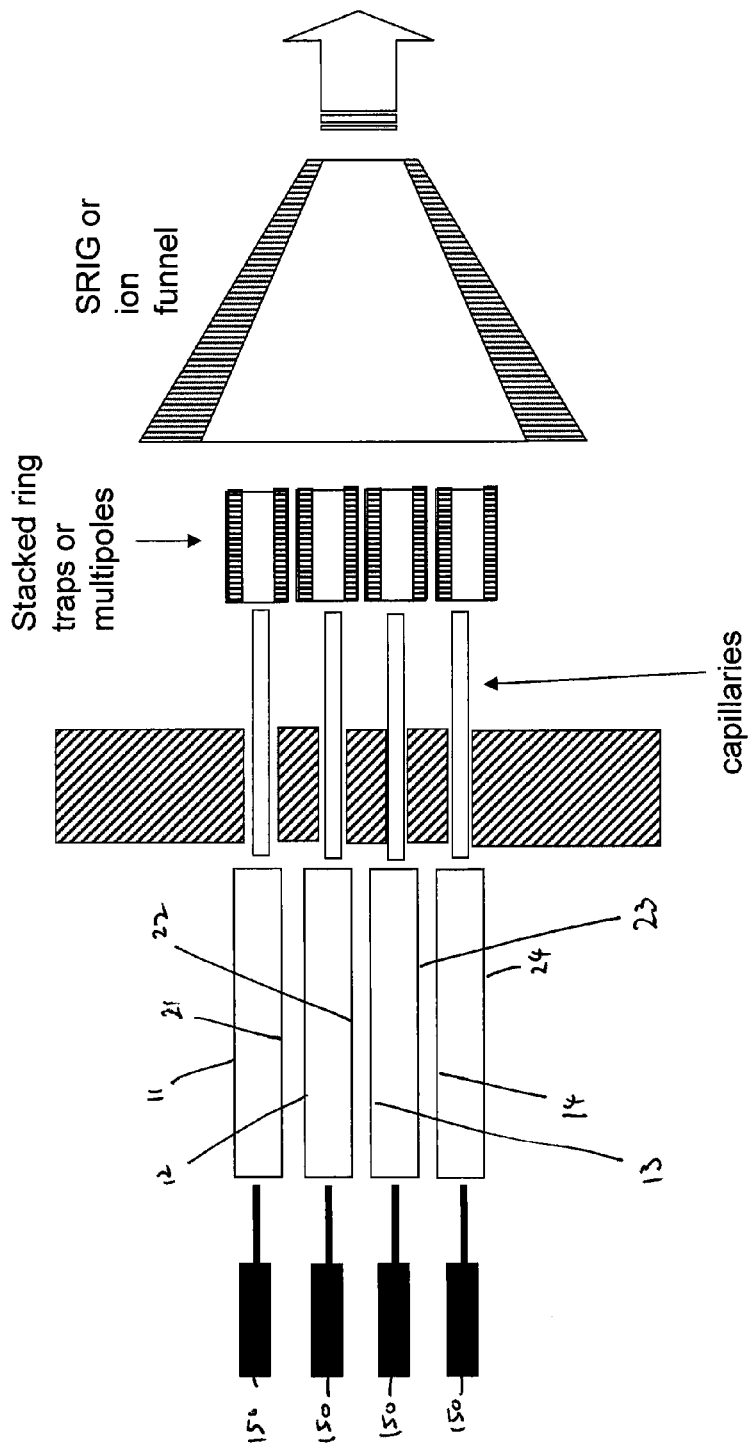
FIG. 14 shows a plurality of FAIMS devices each with its own ion source in combination with stacked ring traps or multipoles and a stacked ring ion guide (SRIG) or ion funnel.

FIG. 14 shows a variation on the devices of FIGS. 12 and 13 but having four ion sources 150, a four channel FAIMS device, four capillaries as well as four stacked ring tracks and a stacked ring ion guide or ion funnel. The stacked ring traps are used to store isolated species from each compensation voltage and/or dispersion voltage derived in the FAIMS device and send them sequentially to the stacked ring ion guide or ion funnel.

Figure 15:
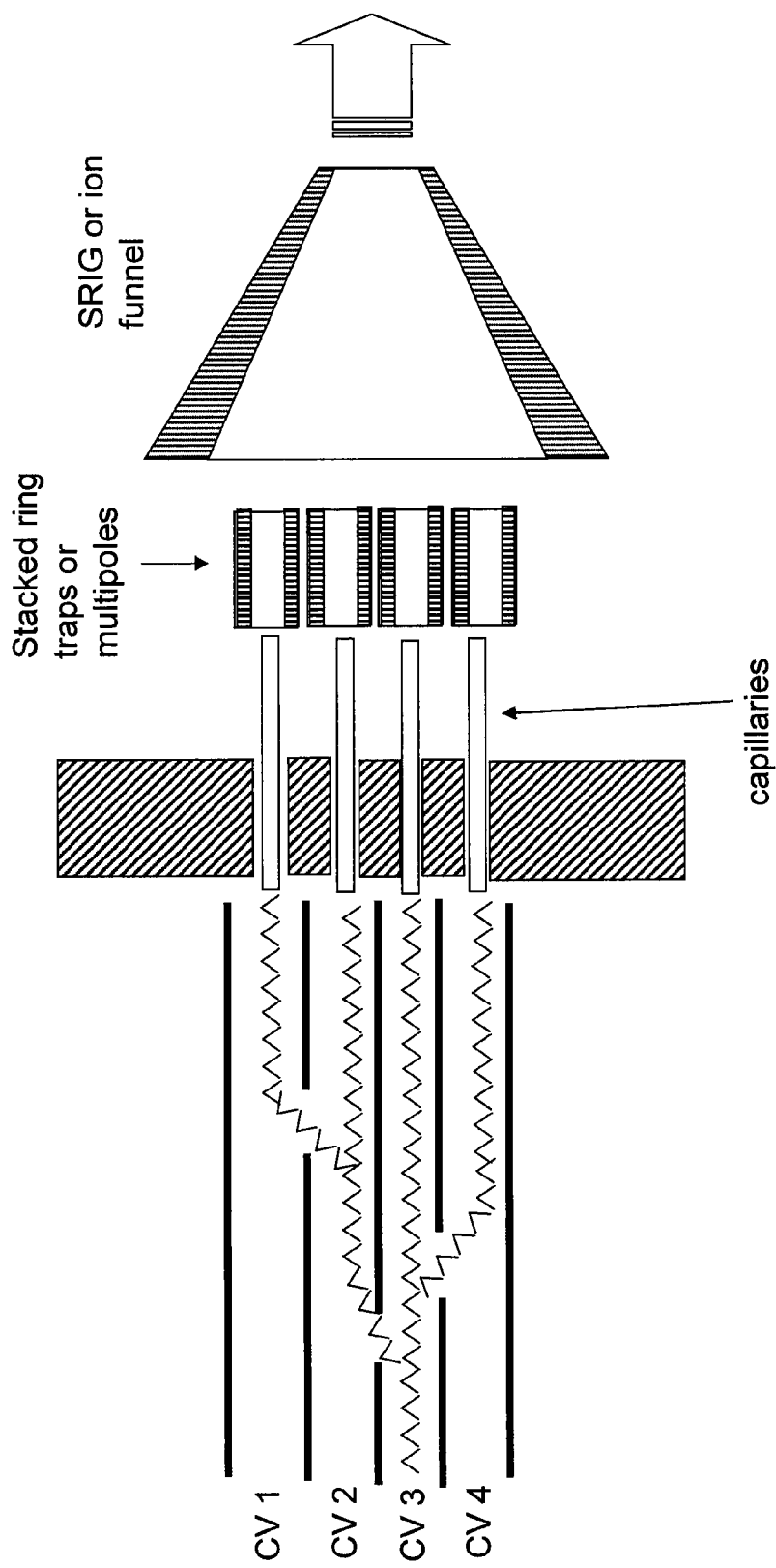
FIG. 15 shows a plurality of FAIMS devices with a single ion source.

A further variation is shown in FIG. 15. This is similar to the arrangement of FIG. 14 but there is only a single ion source 150 and the channels comprise apertures which allow ions to pass between adjacent channels. A single flow of ions from the single ion source passes into one of the channels (having applied compensation voltage CV 3) and is allowed to branch out into multiple channels by allowing selected ions to pass to an adjacent channel (having applied compensation voltages CV1, CV2 and CV4, which may be the same or different to CV3 and to each other). This allows for increased opportunity for selection and detection by comparison with other arrangements which simply allow ions to be lost through attraction to a channel wall.

Figure 16:
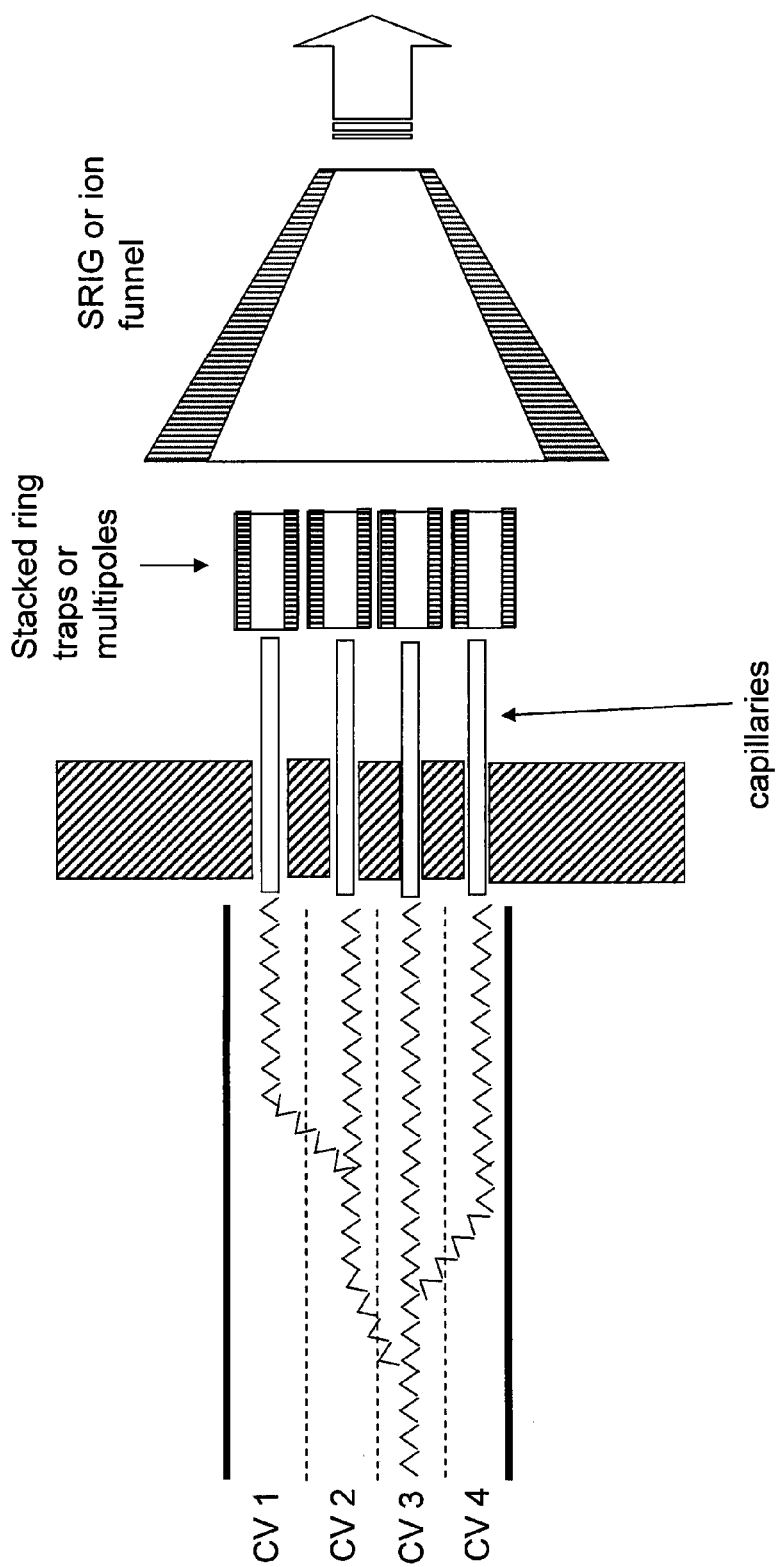
FIG. 16 shows a variation on the arrangement of FIG. 15 wherein partitioning between different FAIMS channels is provided by a layer of wires placed longitudinally.

A still further variation is shown in FIG. 16. This is similar to that shown in FIG. 15 but instead of having a small number of apertures designed to allow ions to pass between channels, wire layers are used to define the channels. The wire layers allow ions to cross to an adjacent channel at any point rather than through discretely placed apertures.

Embodiments comprising different combinations of the features disclosed herein with respect to different embodiments are interchangeable. For example, segmentation of electrode assemblies may be present in any of the embodiments which are not shown to have a segmented electrode. In addition, having different radii of curvature of two opposed electrodes may be employed in any of the other embodiments.

Furthermore, any of the disclosed arrangements having multiple ion sources or splitting a flow of ions from a single ion source into multiple channels might be equally applicable to the other disclosed arrangements including the helical FAIMS devices, the segmented FAIMS devices, and the FAIMS devices having different radii of curvature of two opposed electrodes.

The invention claimed is:

1. An apparatus for separating ions comprising:
    an elongate ion separation channel defined by a plurality of channel walls for constraining ions within the said channel, a first channel wall comprising a first ion separation electrode assembly and a second channel wall comprising a second ion separation electrode assembly and being spaced from the said first ion separation electrode assembly in a direction transverse to a direction of elongation of the channel; and
    a power supply for applying a periodic asymmetric potential to at least one of the first and second ion separation electrode assemblies in order to generate a periodically asymmetric electric field in the channel such that ions flow along the direction of elongation of the channel and are caused to separate according to differential ion mobility;
    wherein the ion separation channel walls define an ion separation channel which is substantially of helical shape.

2. The apparatus of claim 1, wherein the channel walls further comprise an ion focusing electrode assembly of substantially helical shape.

3. The apparatus of claim 2 wherein at least one of the first and the second ion separation electrode assembly is substantially cylindrical.

4. The apparatus of claim 1 wherein at least one of the first and the second ion separation electrode assembly is of substantially helical shape.

5. The apparatus of claim 4 wherein said helical shape is of constant radius.

6. The apparatus of claim 4 wherein said helical shape is of varying radius.

7. The apparatus of claim 6 wherein at least one of the first and the second ion separation electrode assembly is of substantially conical or frustoconical shape.

8. The apparatus of claim 1 wherein the first and second ion separation electrode assemblies are substantially coaxial and the first ion separation electrode assembly is arranged radially within the second ion separation electrode assembly.

9. The apparatus of claim 1 wherein the first and second ion separation electrode assemblies are substantially coaxial and the second ion separation electrode assembly is arranged radially within the first ion separation electrode assembly.

10. The apparatus of claim 1 wherein the first and second ion separation electrode assemblies form walls of the channel such that a field generated by the first and second ion separation electrode assemblies causes the ions to be focused in a direction generally perpendicular to the direction of flow of ions in the channel.

11. The apparatus of claim 3 wherein the ion focusing electrode assembly forms walls of the channel such that a field generated by the ion focusing electrode assembly causes the ions to be focused in a direction generally perpendicular to the direction of flow, of ions in the channel.

12. The apparatus of claim 10 wherein the ion focusing electrode assembly forms walls of the channel such that a field generated by the ion focusing electrode assembly causes the ions to be focused in a direction generally perpendicular to the direction of flow of ions in the channel and wherein the direction of focusing provided by the ion focusing electrode assembly and the direction of focusing provided by the ion separation electrode assemblies are substantially perpendicular.

13. The apparatus of claim 11 wherein:
the ion separation electrode assemblies have a width which extends in a first direction in a plane orthogonal to the direction of flow of ions; and
the ion focusing electrode assembly has a width which extends in a second direction in said plane,
wherein the first direction and the second direction are substantially perpendicular.

14. The apparatus of claim 1 wherein:
the first ion separation electrode assembly has a width which extends in a plane orthogonal to the direction of elongation of the channel,
the second ion separation electrode assembly has a width which extends in a plane orthogonal to the direction of elongation of the channel and
wherein a distance separating the said first and second ion separation electrode assemblies varies in that plane.

15. The apparatus of claim 3 wherein the ion focusing electrode assembly comprises first and second ion focusing electrodes.

16. The apparatus of claim 3 wherein the ion focusing electrode assembly has a curved cross section such that the ion separation channel is of a partially toroidal helical shape.

17. The apparatus of claim 1 wherein at least one of the first and second ion separation assemblies comprises a plurality of segments, wherein at least two of the segments are electrically isolated from each other.

18. The apparatus of claim 17 wherein the segmented ion separation assembly has a time dependent dispersion voltage (DV) and/or compensation voltage (CV) applied to it.

19. The apparatus of claim 17 wherein the helical shaped ion separation assembly is segmented.

20. The apparatus of claim 3 wherein the ion focusing electrode assembly is configured to act as Matsuda plates.

21. A method for separating ions comprising:
directing ions in a gas flow through an ion separation channel of substantially helical shape, the channel being formed between first and second ion separation electrode assemblies spaced apart from each other; and
applying a periodic asymmetric potential to at least one of the first and second ion separation electrode assemblies such that the ions become separated by differential ion mobility in a periodically asymmetric electric field applied between the first and second ion separation electrode assemblies as a consequence of the asymmetric potential.

22. The apparatus of claim 12 wherein:
the ion separation electrode assemblies have a width which extends in a first direction in a plane orthogonal to the direction of flow of ions; and
the ion focusing electrode assembly has a width which extends in a second direction in said plane,
wherein the first direction and the second direction are substantially perpendicular.

* * * * *